US007641823B2

(12) United States Patent
Foster et al.

(10) Patent No.: US 7,641,823 B2
(45) Date of Patent: Jan. 5, 2010

(54) SYNTHESIS OF SMALL PARTICLES

(75) Inventors: Neil Russell Foster, Stives (AU);
Hubert Leonardus Regtop, Mittagong (AU); Fariba Dehghani, Rosebery (AU)

(73) Assignee: MAP Pharmaceuticals, Inc., Mountain View, CA (US)

( * ) Notice: Subject to any disclaimer, the term of this patent is extended or adjusted under 35 U.S.C. 154(b) by 853 days.

(21) Appl. No.: 10/497,715

(22) PCT Filed: Dec. 6, 2002

(86) PCT No.: PCT/AU02/01657

§ 371 (c)(1),
(2), (4) Date: Mar. 23, 2005

(87) PCT Pub. No.: WO03/047553

PCT Pub. Date: Jun. 12, 2003

(65) Prior Publication Data

US 2005/0163723 A1 Jul. 28, 2005

(30) Foreign Application Priority Data

Dec. 7, 2001 (AU) .................................... PR9382

(51) Int. Cl.
*B29B 9/00* (2006.01)
(52) U.S. Cl. ................................. 264/13; 264/5; 425/6
(58) Field of Classification Search .................. None
See application file for complete search history.

(56) References Cited

U.S. PATENT DOCUMENTS

| 5,851,453 | A | * | 12/1998 | Hanna et al. ................... 264/5 |
| 6,063,910 | A | | 5/2000 | Debenedetti et al. |
| 2003/0013634 | A1 | * | 1/2003 | Foster et al. .................. 514/1 |
| 2004/0081626 | A1 | * | 4/2004 | Watanabe et al. ............. 424/46 |

FOREIGN PATENT DOCUMENTS

| GB | 2 322 326 A | 8/1998 |
| WO | WO 95/01221 | 1/1995 |
| WO | WO 97/31691 | 9/1997 |
| WO | WO 00/37169 | 6/2000 |
| WO | WO 01/43845 A1 | 6/2001 |
| WO | WO 01/49407 A1 | 7/2001 |
| WO | WO 02/45690 A1 | 6/2002 |

* cited by examiner

*Primary Examiner*—Mary Lynn F Theisen
(74) *Attorney, Agent, or Firm*—DLA Piper LLP (US)

(57) ABSTRACT

The invention provides an apparatus for forming fine particles of a substance in a precipitation chamber, in which the apparatus has means to convey the fine particles from the precipitation chamber to at least one particle collection chamber, downstream of the precipitation chamber, the particle collection chamber having an inlet and an outlet separate from the inlet. The invention also provides a method of forming fine particles of a substance, the method comprising contacting a non-gaseous fluid containing the substance with a dense fluid to expand the non-gaseous fluid in a precipitation chamber, conveying a resulting mixture of fluid and the fine particles from the precipitation chamber to a collection chamber, the collection chamber having an inlet and an outlet separate from the inlet.

18 Claims, 6 Drawing Sheets

SYNTHESIS OF SMALL PARTICLES

CROSS REFERENCE TO RELATED APPLICATIONS

This application claims the benefit of priority under 35 USC §119(a)-(d) of International Application No. PCT/AU02/01657, with an international filing date of Dec. 6, 2002, which claims priority to Australian Application No. PR 9382, filed Dec. 7, 2001, which is incorporated herein by reference in its entirety.

FIELD

The present invention relates to a method for forming and collecting fine particles of a substance, such as a pharmaceutical or biological substance, by anti-solvent precipitation, particularly but not exclusively suitable for administration to organisms. The invention also relates to fine particles of biological substances produced by the method and to compositions, particularly pharmaceutical compositions, containing an active substance.

BACKGROUND

Throughout this specification, unless stated otherwise, where a document, act or item of knowledge is referred to or discussed, this reference or discussion is not an admission that the document, act or item of knowledge, or any combination thereof, at the priority date, was part of the common general knowledge.

Production of uniform micron size particles (or within a narrow size range) of fragile molecules such as proteins is a challenge in the pharmaceutical industry. One use of fine particles is pulmonary absorption of drugs. This is an important route of entry for many indications including some pulmonary diseases, for example, bronchial asthma. One advantage of this mode of administration is that access to the circulation is rapid, because the surface area is large. As well as almost instantaneous absorption of the drug into the blood, delivery to the lung has the advantages of avoidance of hepatic first-pass loss, and in the case of pulmonary disease, local application at the desired site of action.

Delivery to the lung may also provide an alternative for the treatment of conditions that have traditionally been treated by systemic administration of a drug. The administration of proteins is a case in point. Insulin is currently administered by injection because it is not stable in the gastrointestinal tract. Diabetic patients need to self-administer several injections. However, there is a lack of compliance with the use of injections because of the associated inconvenience and pain. Administration of the protein to the lung is more likely to be accepted by such patients and is therefore an attractive alternative to injections, as long as the protein can be formed as fine particles, without significant loss of biological activity. Usual criteria for the use of aerosol delivery for the administration of therapeutic drugs to the lung are that the drug is in particulate form with the particles having a size in the range of about 0.05-10 μm, preferably 1-5 μm while (obviously) retaining biological activity, which often requires the substance's structure to be maintained. A common problem in manufacture of such particles is unacceptable variation in particle size.

Drugs in the form of fine particles are also suitable for use in the area of oral, controlled or sustained release delivery. One application of such technology is in the case of a drug in which there is a small difference in dosage levels between the drug being effective and being toxic. In the latter technology, it is also important that the particles have a uniform particle size.

Another application of fine particles of pharmaceuticals is transdermal drug delivery. Apart from traditional sub-cutaneous, intravenous, etc. injection, new methods of administration are being used, such as lasers to create a fine channel through the skin for drug delivery. A similar mechanism involving high-pressure drug delivery transdermally is also being used. Thus, the applications for fine or micron-sized pharmaceutical particles are increasing.

Dense gas techniques utilizing fluids, near or above their critical point, as a solvent or anti-solvent have been developed in recent years. Two dense gas methods have been considered for the production of solid particles. The first method is known as the Rapid Expansion of Supercritical Solutions (RESS), and involves expanding a supercritical solution of the material of interest through a nozzle. Whilst providing an effective method for producing some fine particles, the applicability of the RESS method is limited by the low solubility of proteins in dense carbon dioxide.

The second method, known as the gas anti-solvent process, involves rapidly precipitating solutes from organic solutions, typically using dense carbon dioxide as an anti-solvent. The anti-solvent expands the solution, thereby decreasing the solvation power of the solvent, and eventually resulting in the precipitation of the solute.

Gas anti-solvent processes have been utilized for the generation of micron-sized particles in two modes. The first mode, known simply as the gas anti-solvent process (GAS), involves the gradual addition of an anti-solvent to the organic solution containing the solute until the precipitation occurs. The second mode, known as the Aerosol Solvent Extraction System (ASES), involves continuous introduction of a solution containing the solute of interest through a nozzle into a flowing dense gas stream. As the solution is sprayed in to the dense gas, high degrees of supersaturation result in the precipitation of fine particles. In general, precipitation using this process is rapid and requires mild operating temperatures and pressures.

The GAS process has been attempted for the generation of micron-sized particles of insulin, lysozyme, and peroxidase. The difficulty of applying these techniques to the production of micronised particles of pH sensitive proteins is that they involve exposure of the protein to organic solvents, the latter being potential denaturants. This would, for example, inactivate insulin. Organic solvents are also undesirable as they are more difficult to dispose of. Thus, this process is largely unsuitable.

In one attempt to overcome this limitation, a form of the ASES process has been developed, referred to as Solution Enhanced Dispersion by Supercritical Fluid (SEDS). SEDS involves using the ASES process but with a special coaxial nozzle which, in part, overcomes the problem of exposure to organic solvents.

Current apparatus utilising these processes, particularly ASES, for the production and collection of particulate products comprise a precipitator and a collection device in the same chamber. The solution containing the product of interest and the anti-solvent (which contains the dense gas and, optionally, a modifier) are passed through the precipitation chamber co-currently. As the particles are formed, they fall to the bottom of the collection device under gravity and can become compacted, aggregated (physical association) or agglomerated (chemically bonded). The particles can also become further compacted during the washing stage at the end of the process, due, for example, to the high pressure and high flow-rate of the dense gas anti-solvent.

Aggregation occurs when a collection of two or more particles are held together by weak cohesive forces, such as van der Waal's forces. Aggregates can be dispersed with shear forces and/or solvents. Agglomeration on the other hand, occurs when a collection of two or more particles are held together by strong inter-particle forces such as crystal bonds. Agglomerates are more difficult to break up and disperse.

In small particle formation processes, it is desirable to avoid the particles becoming agglomerated or compacted, since it is more difficult to break this material up, particularly while avoiding damage to the active component. The particles resulting from such processes are, therefore, not uniform in size and shape, which is not ideal for the use of such particles in pharmaceutical applications. However, some degree of aggregation may be desirable in some situations where the particles produced are too fine to be collected. The fine powders that have not become aggregated may be washed out of the system, resulting in a low yield. Aggregation between particles makes the particles larger and easier to collect, and after collection the aggregate can be broken up by mechanical force.

Particles to be used for the pulmonary delivery of pharmaceuticals should ideally be less than 5 to 10 µm in diameter. Particles of this size are more easy to aerosolise, and when inhaled, these particles are easily able to reach the lungs. However, when particles become compacted in the collection chamber, the mass fraction of particles with a diameter of less than 5 μm (and thus suitable for pulmonary delivery) is low.

Collection processes using known single-stage apparatus are essentially batch processes with short run times, due to the necessity of regularly stopping the run to remove the precipitated particles before caking (ie, aggregation of a mass of fine particles which may form a block to a chamber's outlet) occurs. The production of particles using such apparatus is thus, necessarily, a batch-wise process. The process is therefore inefficient and there can be poor yields and recovery of the product.

The invention is directed towards an apparatus for particle formation which operates in a more efficient manner (ie, increase the yield of fine particles collected relative to starting materials) and does not damage the particles that are formed using the apparatus or substantially increase the average particle size collected.

SUMMARY OF THE INVENTION

In a first aspect, the present invention provides an apparatus for forming fine particles of a substance in a precipitation chamber, in which the apparatus has means to convey the fine particles from the precipitation chamber to at least one particle collection chamber, downstream of the precipitation chamber, the particle collection chamber having an inlet and an outlet separate from the inlet. In one embodiment, the outlet is disposed above the inlet in use of the apparatus, such that gravity exerts a force generally towards the inlet on particles adjacent the outlet.

The particles are formed by contacting a non-gaseous fluid containing the substance with a dense fluid to expand the non-gaseous fluid in the precipitation chamber.

In a further form of the invention, the apparatus further includes at least two particle collection chambers in parallel with each other and each able to be connected in series with the precipitation chamber.

The invention also provides a method of forming fine particles of a substance, the method comprising contacting a non-gaseous fluid containing the substance with a dense fluid to expand the non-gaseous fluid in a precipitation chamber, conveying a resulting mixture of fluid and the fine particles from the precipitation chamber to a collection chamber, the collection chamber having an inlet and an outlet separate from the inlet.

In one embodiment, the method is conducted wherein the fine particles flow with the dense gas from a first chamber in which the particles are formed to a second collection chamber, from which the particles are collected. Preferably, the second collection chamber has an inlet and an outlet separate from the inlet, in which the fine particles and dense fluid pass through the inlet and the flow of dense fluid through the outlet is adjusted to maximise the proportion of fine particles collectable from the second collection chamber.

In an aspect of the invention, there is provided an apparatus wherein the precipitator and the collector are two separate chambers, in which fine particles (with a narrow particle size distribution) can be produced which are less affected by the problems of compaction, agglomeration and aggregation, while still being collectible in an adequate yield. In addition, where the particles are finer than particles produced using prior art apparatus, and the mass fraction of particles with a diameter of <5 μm is higher than in prior art apparatus, an adequate yield is obtainable. Also, an essentially batch process can be made semi-continuous.

In another aspect, the invention provides an apparatus for the methods described above. In particular, there is provided an apparatus for forming fine particles including:

a precipitation chamber in which the dense fluid and non-gaseous fluid containing the substance are contacted so as to precipitate the fine particles; and at least one particle collection chamber, downstream of the precipitation chamber from which the fine particles are collected.

Preferably, the particle collection chamber has an inlet and an outlet separate from the inlet, in which the fine particles and dense fluid pass through the inlet and the flow of dense fluid through the outlet is adjusted to maximise the proportion of fine particles collectable from the second collection chamber.

It is also desirable for the apparatus to include at least two particle collection chambers in parallel to be used alternately, each in series with continuous use of the precipitation chamber in a fill-empty-fill-empty cycle.

In one embodiment, within the collector device or collection chamber, the particles are largely suspended by the force exerted on them by a flow of dense gas in one direction, which force is generally balanced by a second force. This second force may be gravity (ie, the particles' weight) where the collection chamber is orientated such that the outlet is above the inlet when the collection chamber is connected to (or on-line with) the particle formation apparatus. Such a force could also be generated by other means, eg. centrifugal force with an appropriate arrangement of the collection chamber(s), and such an arrangement would allow variation of this second balancing force. Where the particles are charged, electromagnetic forces may be employed. As will be appreciated by one skilled in the art, the objective is to balance the force on particles of the carrying fluid, which otherwise tends the particles either to "cake" at one end of the collection chamber and/or to escape through the outlet with the carrying fluid.

Therefore, the newly formed particles do not "fall" on top of the previously formed particles and are not subjected to a pressure which could deform their shape and are also less susceptible to aggregation.

Further, the use of such an apparatus allows higher yield and recovery of particles per run, the ability to process more material per run with longer run times, all of which lead to a more efficient process and greater production capacity.

Such an apparatus can be readily scaled up to process larger amounts of material.

The anti-solvent used in the method of the invention should be a neutral solvent and/or a solvent of relatively low polarity. Suitable solvents include a $C_{1-4}$ alkane gas, a $C_{2-4}$ alkene gas, a $C_{2-4}$ alkyne gas, hydrofluorocarbons, refrigerants, like RF134a, and some organic solvents, such as hexane, or two or more thereof. In one embodiment, the anti-solvent is an alkane gas. Ethane is a particularly preferred anti-solvent. Preferably, the anti-solvent does not significantly alter the pH of the non-gaseous fluid.

The method of the present invention is capable of producing fine particles of the substance, and is particularly useful for the production of fine particles of pH sensitive substances and biologically active substances, since the biological activity of such substances may be retained. The present method is also particularly suited to water soluble substances. The non-gaseous fluid is an aqueous solution in one embodiment.

The modifying agent may be present in an amount sufficient to absorb substantially all of the non-gaseous fluid of the non-gaseous fluid-biologically active substance solution. The modifying agent may be any substance that modifies the polarity of the anti-solvent and acts as an extractant for (ie. solvent for) the non-gaseous fluid. The modifying agent may be selected from the group consisting of $C_{1-6}$ alkanols, $C_{1-6}$ thiols and $C_{1-6}$ amines. Preferably, the modifying agent is ethanol.

In one embodiment of the invention, the anti-solvent/modifying agent combination is ethane/ethanol.

In another aspect, the invention provides smaller particles than are possible from the prior art by use of a neutral anti-solvent modified by a modifier to change its polarity by using a separate collection chamber in a "dual stage" process, particularly where most of the newly formed fine particles are suspended within the chamber by the force of the dense fluid flowing through the chamber accommodating the particles being balanced by gravity in the opposite direction, to reduce aggregation and agglomeration of the particles.

The dense gas can be at various temperatures and pressures. Preferably the temperature of the dense gas is in the range of $-20°$ C. to about $100°$ C., most preferably about $5°$ C. to about $45°°$ C. The lower temperatures result in increased viscosity an reduced mass transfer properties, and this reduces efficiency of the method. High temperatures are more costly to run and may damage the substance. Preferably the dense gas has a pressure in the range of about 1 bar to 400 bar. A pressure between about 5 to 200 bar is particularly preferred. Most preferably, the pressure of the dense gas is such as to maintain the mixture of solvent, anti-solvent and modifying agent as a single phase which reduces loss of precipitate which may remain dissolved in a second phase, and be washed from the system.

Preferably, both the anti-solvent gas and the modifier are substantially inert to the pH-sensitive, biologically active substance.

The particles produced by the method of the invention may also include delivery agents such as liposomes, lipids (including phospholipids), water soluble polymers, controlled-delivery coatings, surfactants, phytosterols, and any other delivery agents known in the art.

Preferably, at least half, and more preferably substantially all, of the fine particles produced by the method of the invention have a particle size less than 10,000 nm. More preferably, the fine particles have a size no greater than 6,500 nm. Particles having a size in the range of up to 5,000 nm are particularly useful for administration to the lung. If smaller particles are desired, it is believed that the method of the present invention can produce particles down to nanometre size, although such particles can be more difficult to collect and naturally aggregate into larger particles.

The solution of the active substance may be contacted with dense gas in any suitable manner. Preferably, the solution is introduced as droplets into the dense gas. For example, the solution and dense gas may be contacted by concurrently spraying the two through a nozzle or the like. Alternatively, the solution may be sprayed through the dense gas. A further option is to pass the solution concurrently or countercurrently with respect to a stream of the dense gas. The solution may be passed through a continuum of the dense gas in the form of a thin film or plurality of streams.

Preferably the method of the invention is carried out using the ASES process. The term "pH-sensitive, biologically active substance", as used throughout the specification, refers to any natural or synthetic substance which possesses a biological activity such as, for example, an enzymatic activity, channel function (e.g. ion channel), receptor or binding function, hormonal or neurotransmitter activity, or other pharmacological activity, or a protein, polypeptide, peptide, peptide analog or peptidomimetic, or nucleic acid or nucleic acid in association with a protein, polypeptide or peptide, which is adversely affected by pH outside of the normal physiological pH range (e.g. 6.8 to 7.5), especially low pH (e.g. less than 5.0). The adverse affect upon the biological activity caused by the pH may be the result of, for example, degradation, cleavage or conformational changes in the substance or inactivation of an active site or binding domain.

The pH-sensitive, biologically active substance is preferably selected from the group consisting of an antimicrobial agent, virus, antiviral agent, antifungal pharmaceutical, antibiotic, nucleotide, DNA, antisense DNA, RNA, antisense RNA, amino acid, peptide, protein, enzyme, hormones, immune suppressant, protease inhibitors, thrombolytic anticoagulant, central nervous system stimulant, decongestant, diuretic vasodilator, antipsychotic, neurotransmifter, sedative, anaesthetic, surfactant, analgesic, anticancer agent, antiinflammatory, antioxidant, antihistamine, vitamin, mineral, sterol, phytosterol, lipid and esters of fatty acids.

More preferably, the pH-sensitive, biologically active substance is selected from proteins, polypeptides, peptides, peptide analogs or peptide mimetics. Most preferably, the pH-sensitive, biologically active substance is selected from the proteins insulin, erythropoetin, calcitonin, LHRH, somatostain, epidermal growth factors, DNase platelet derived growth factors, interleukins, interferons, cytokines, peptides of immunoglobulins, TNF and other biologically active peptides, monoclonal antibodies based on TNF inhibitors as well as antibodies based on inhibitors of cytokines and interleukins.

In a second aspect, the present invention provides a pharmaceutical composition comprising particles of a biologically active substance produced by the method of the present invention.

The pharmaceutical composition is preferably in a form suitable for inhalation delivery, for example, for delivery by a metered dose inhaler or a nebuliser. Further, a transdermal delivery system may be used (eg, recent devices involving laser-generated or high-pressure dermal channels) and more traditional parenteral administration.

In a third aspect, the present invention provides a method of treatment of a subject, the method comprising administering to the subject, an effective amount of particles of a biologically active substance produced by the method of the present invention.

The method of the third aspect may be the treatment of insulin-dependent diabetes by administration of insulin particles produced by the method of the present invention.

In the description, the term "dense gas" means a fluid substantially near or above its critical pressure (Pc) and temperature (Tc). In practice, the pressure of the fluid is likely to be in the range (0.5-1.5)Pc and its temperature (0.5-1.2)Tc.

It will be understood that the term "comprises" (or its grammatical variants) as used in this specification is equivalent to the term "includes" and should not be taken as excluding the presence of other elements or features.

The method of the present invention, in its preferred forms, may provide one or more of the following advantages:
1. The ability to produce and collect significant yields of fine powders of proteins and other pharmaceuticals with narrow particle size distributions.
2. The ability to use aqueous solutions thereby enabling concentrated solutions of material to be processed with minimal risk of deactivation of biological activity. Aqueous solutions are also easier and cheaper to handle.
3. The use of one of the preferred anti-solvents, ethane, overcomes the problems associated with an acidic pH environment for proteins and other pH sensitive or acid-labile molecules (ethane is neutral).
4. The use of an organic compound such as ethanol as the modifier in the ethane phase appears to enhance the morphological characteristics of the powders produced, including insulin. While not wishing to be bound by any particular theory, it appears that the morphological characteristics of the powders produced are also dependent on the relative concentrations of the solutions at the time of contact, the time period that the solutions are in contact with each other, and the time period that the particles are in contact with each other after precipitation. These variables can be adjusted during use of the method to optimise results.
5. The ability to use a substance such as ethanol as a modifier for the anti-solvent as described in 3 above, yet produce fine particles of a biologically active substance in which 98 to 100% biological activity has been retained.
6. The ability to introduce an additional component in either the solvent stream or the modified anti-solvent stream, which when co-precipitated with the protein or pharmaceutical will enhance dissolution rates and/or bioavailability.
7. The ability to process materials at temperatures below those required for supercriticality, thereby reducing the risk of thermal degradation.
8. The ability to work at lower pressures than that claimed in the prior art, thereby reducing the potential cost of the process. In order that the invention may be more readily understood, we provide the following non-limiting embodiments as examples.

While suitable for any of the proteins mentioned above, the examples illustrating the invention are described using insulin as the desired active ingredient. Similarly, for the purposes of illustration, the examples describe the use of ethane as the anti-solvent and ethanol as the modifier. Low endotoxin bovine insulin (lyophilized powder of 28.5 USP units/mg, lot No. 47H0573) and sodium hydroxide were purchased from Sigma Chemicals and used as received and dissolved in deionised water. Liquid carbon dioxide and ethane (Industrial Grade 99.95%) were purchased from BOC Gases.

Figure 7:
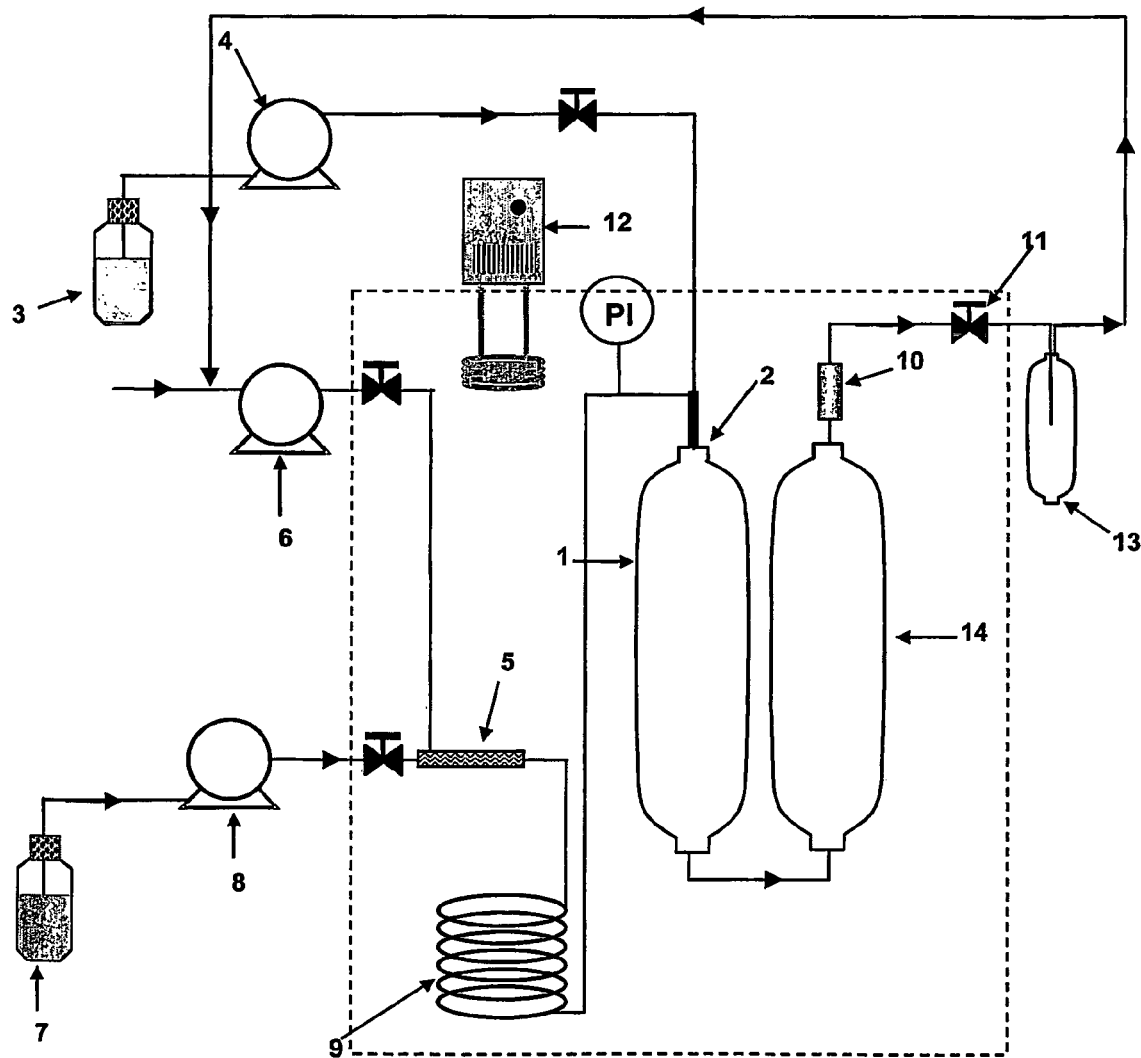
FIG. 7 illustrates an industrial scale embodiment of the invention similar to that in FIG. 1, having a separate particle collection chamber, also called a "dual stage" apparatus.

The set-up for the ASES apparatus (FIGS. 1, 7 and 8) was designed to improve the proportion of fine particles generated of the drug, which could be collected as such, and increase the yield and recovery of the product. In order to minimize compaction and increase the fine particle mass (FPM) fraction of the precipitate, a dual precipitation and collection chamber arrangement with no filter between the precipitation and collection chambers was used. The precipitates and anti-solvent pass co-currently from the precipitation chamber to the (second or downstream) collection chamber. The embodiment in FIG. 8 has two "parallel" collection chambers to enable continuous (rather than batch) operation by alternating between the two collection chambers.

Figure 1:
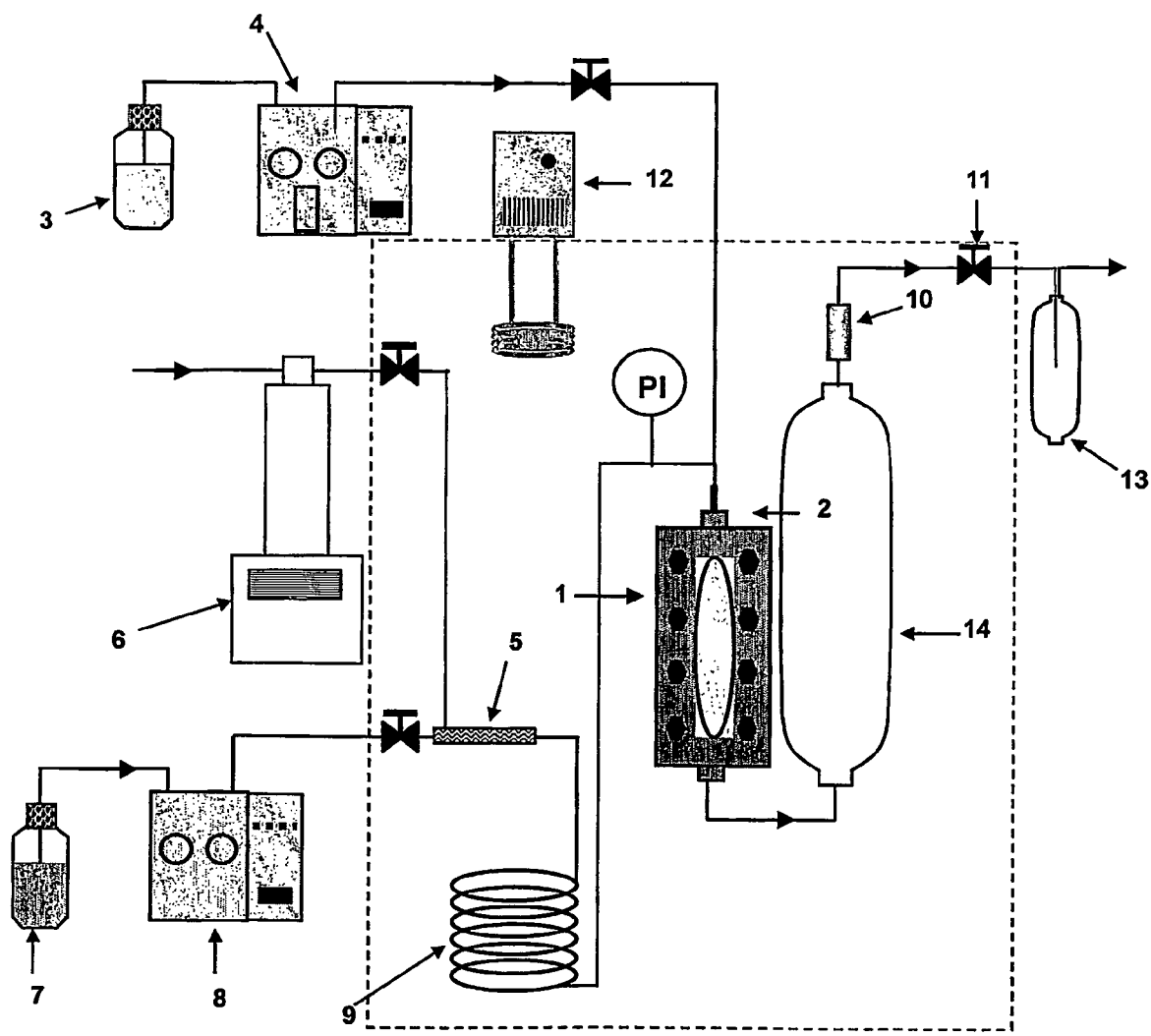
FIG. 1 illustrates a laboratory scale embodiment of the invention, having a separate particle collection chamber, called a "dual stage" apparatus.
Figure 2:
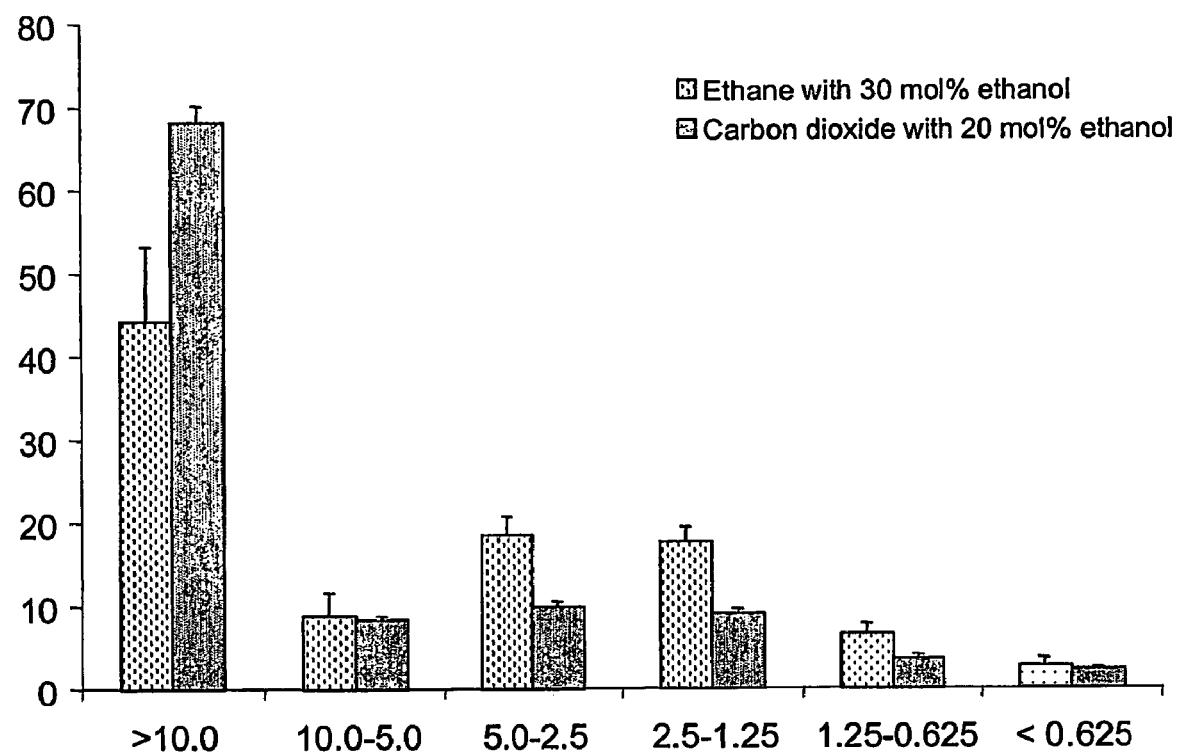
FIG. 2 shows a graph comparing the aerodynamic particle size distribution of insulin particles precipitated at 25° C. and 150 bar using 20 mol % ethanol in carbon dioxide and 30 mol % ethanol in ethane.
Figure 3:
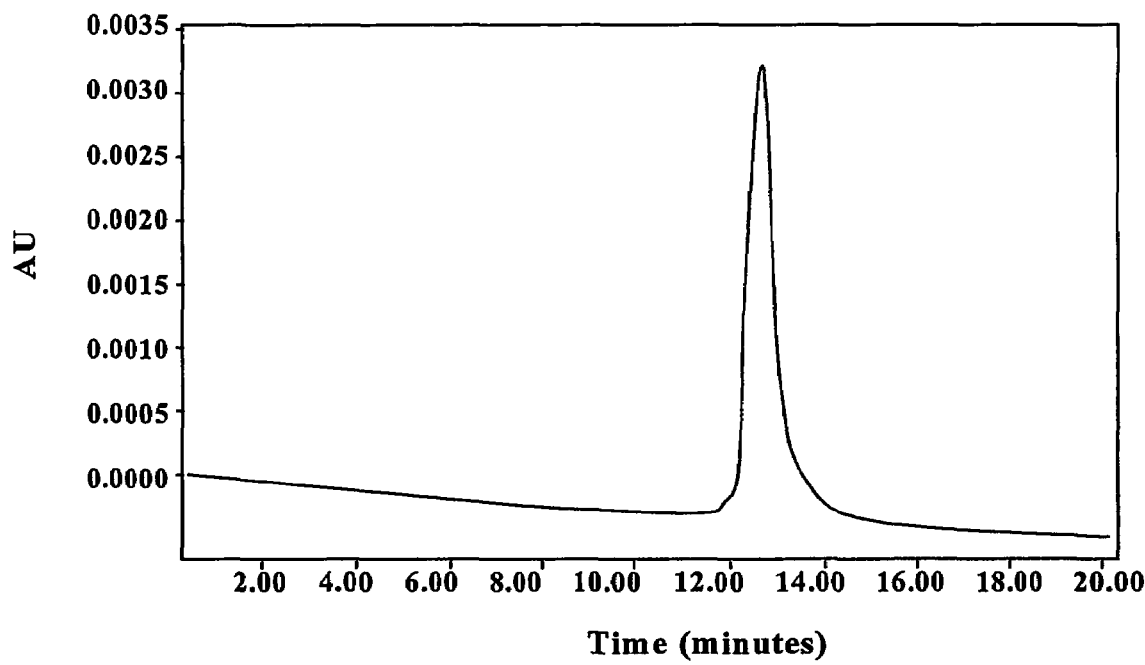
FIG. 3 shows an HPLC chromatogram of the insulin monomer.
Figure 4:
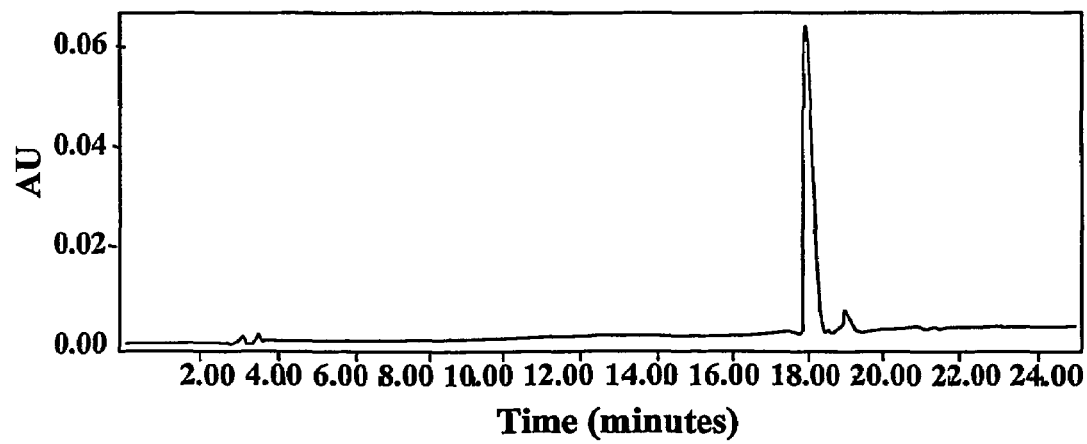
FIG. 4 shows an HPLC chromatogram for the separation of insulin and deamido insulin.
Figure 5:
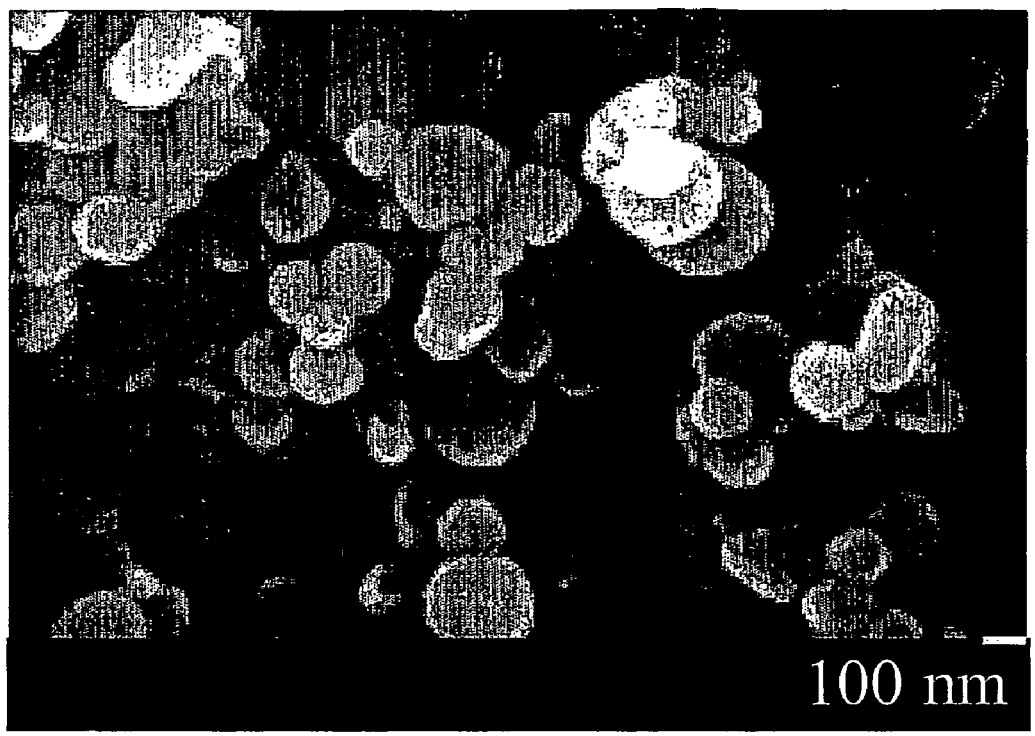
FIG. 5 shows an SEM of insulin particles.

An ASES apparatus used is schematically shown in FIG. 1. The apparatus includes a precipitation chamber 1 which is fitted with a nozzle 2. Through this nozzle is sprayed a solution of the substance of interest and the dense gas and the modifier. The solution of the substance of interest is pumped into the precipitation chamber from the reservoir 3 by means of pump 4. The dense gas is pumped into a static mixer 5 by means of pump 6. The modifier is simultaneously pumped from its reservoir 7 into the static mixer 5 by means of pump 8. The desired mixture of ethanol with ethane is prepared in the static mixer 5. The chamber is first pressurised with carbon dioxide via a syringe pump (ISCO Model 500) 6 to attain a pressure of 20 to 180 bar to maintain the ethane/ethanol mixture as a single phase. The modified ethane is then delivered into the precipitation chamber 1 at the desired processing conditions and $CO_2$ is purged from the system. The operating temperature is controlled to within ±0.1° C. using a temperature controlled water bath heated by heater 12.

On leaving the static mixer, the dense gas/modifier mixture is passed through a cooling coil 9, and then into the precipitation chamber 1. The flow of the fluids continues through the precipitation chamber and to a second high-pressure chamber, the particle collection chamber 14. The flow rate is controlled by the metering valve 11. The apparatus is placed in a water bath, which is heated by the heater 12, to control and maintain the temperature of the precipitation and collection chambers. There is no filter between the two chambers, but a filter is downstream of the particle collection chamber.

The flow of the fluids through the precipitation chamber continues into the collection chamber 14 via its inlet (at the bottom of collection chamber 14 as shown in FIG. 1). The dense fluid then passes through the collection chamber outlet to filter 10. The flow rate is controlled by the metering valve 11. Once passing through the valve, the flow of fluids passes through a cold trap or separator 13, at low temperature, to separate the solvent and modifier from the dense gas. The dense gas can then be recycled through the system.

Once the desired temperature and pressure (namely 25° C. and 150 bar) are achieved in the chamber 1, and the chamber filled with 30 mol % ethanol in ethane mixture, the aqueous solution containing the protein (low endotoxin bovine insulin (lyophilized powder of 28.5 USP units/mg, lot No. 47H0573, purchased from Sigma) is pumped from reservoir 3 at a constant flow rate using a solvent delivery unit (Waters pump, Model 510) 4 and sprayed through a capillary nozzle 2 (50 um internal diameter) into the chamber. The pressure drop through the nozzle was adjusted to about 50 bar by a metering valve 21. This pressure drop can be adjusted to optimise the efficiency of the process. Modified ethane was fed continuously through to the chamber at a constant flow rate that was adjusted with the metering valve 11. The operating conditions, the flow-rate ratio of the aqueous feed and the anti-solvent, and the modifier mole fraction were optimized (using published ternary phase equilibrium data for ethane, ethanol and $CO_2$) so as to have a homogenous (ie, single phase) mixture of dense fluid-ethanol-water in the precipitation chamber.

The mole fraction of ethanol in the anti-solvent was kept at 0.3 and a volumetric flow rate ratio of feed to anti-solvent of 0.4/12 was used in the process. This is primarily adjusted so as to maintain a single homogeneous phase in the system, particularly in the precipitation chamber. The high flow rate of the anti-solvent facilitated the dispersion and mixing of the aqueous spray mist across the chamber resulting in higher rates of water extraction from the droplets.

Micronised particles of proteins with uniform particle size suitable for aerosol drug delivery systems were thus produced from aqueous solution at room temperature in effectively one step. No toxic chemicals were used. Residual ethanol content in the final product was less than 10 ppm. The small particulate material of the present invention is particularly useful in the preparation of pharmaceutical preparations formulated to provide oral, controlled or sustained release, or for inhalation or transdermal administration and conventional modes.

Figure 8:
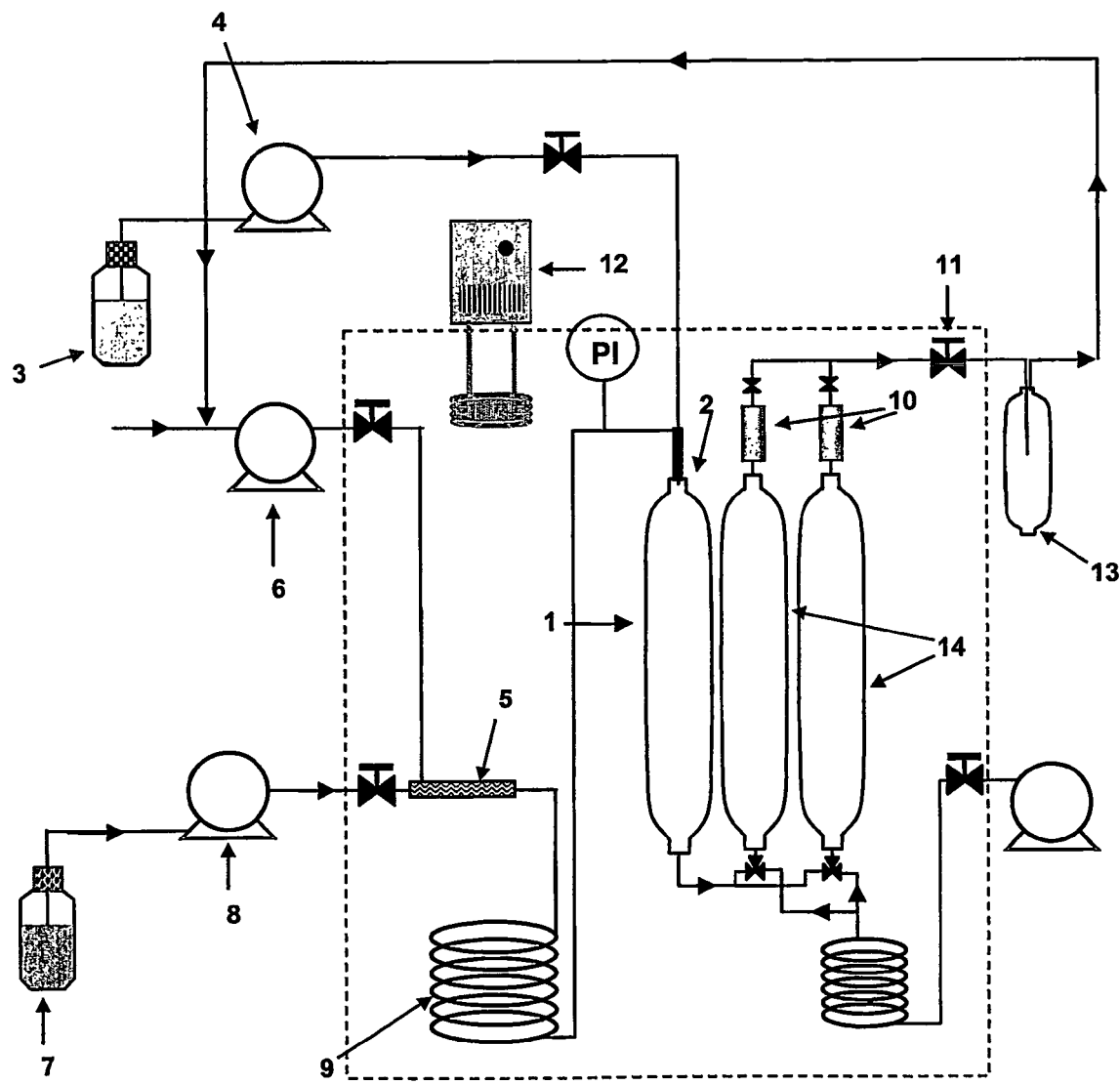
FIG. 8 describes another embodiment of the invention, being an apparatus having more than one particle collection chamber.

FIG. 8 shows a modified design incorporating two particle collection chambers 14. The apparatus operates as described for FIGS. 1 and 7, but once the first particle collection chamber has been filled to optimum capacity for collection of particles, the flow of dense gas containing the formed particles is diverted into a second particle collection chamber. The removal of the particles from the first particle collection chamber can be effected while the apparatus, particularly the precipitation chamber, is still in operation. Once the second particle collection chamber has been filled to capacity, the flow of dense gas containing the precipitated particles can be diverted into a third particle collection chamber, or back to the first particle collection chamber which by this time would have been cleaned out. In this way, the apparatus can operate in a continuous manner for the production of particles.

On the laboratory scale, the view cell (such as a Jerguson sight gauge, model 13-R-32) can be used as a precipitation chamber for visual observation of the precipitation stages as shown in FIG. 1. A coaxial nozzle 2 is connected to the chamber for spraying the solutions and anti-solvent. The nozzle consists of a capillary tube (SGE, PEEK tube 200 mm length, 50 μm i.d., and 1.59 mm o.d.) inserted into a stainless steel tube (Alltech, 2.16 mm i.d. and 3.18 mm o.d.). The three pumps in the system are for the delivery of the protein solution (Waters Model 510), ethanol (Hewlett Packard, series 1050) and anti-solvent such as ethane and $CO_2$ (ISCO Syringe pump 500D). The anti-solvent was mixed with ethanol in line using a static mixer (KOFLO Corporation). The composition of the mixture was adjusted by the flow rate of each pump. The anti-solvent flow rate was controlled by a metering valve at the exit. The ethanol/water/anti-solvent mixture was maintained in a homogeneous phase at the operating pressure and temperature of the process. The carbon dioxide/ethanol mixture was passed through a preheating coil to attain the system temperature. The high pressure chambers were placed in a water bath consist of a thermostatic heater (Thermoline Unistat heater/circulator) to control the temperature. The pressure of the system was monitored with Druck pressure transducers (Model PDCR 911) coupled to Druck pressure indicators. The anti-solvent and solvent were separated after the metering valve and the solvent was collected in a chamber. The filters were placed after the high pressure chambers to collect any remaining fine powder in the line.

Preparation of Particles

The preparation of the particles was carried out using the apparatus represented in FIG. 1 (discussed above). The desired mixture of ethanol with ethane is prepared in the static mixer 5. The chamber is first pressurised with carbon dioxide (which aids apparatus sterilisation) via a syringe pump (ISCO Model 500) 6 to attain a pressure of 20 to 180 bar to maintain the ethane/ethanol mixture as a single phase. The modified ethane is then delivered into the precipitation chamber 1 at a pressure of 140 bar, a temperature of 35° C., and a flow rate of 15 mL/min, and $CO_2$ is purged from the system. The operating temperature (35° C.) is controlled to within ±0.1° C. using a temperature controlled water bath heated by heater 12.

Micronisation by the ASES process was conducted by first placing the high pressure chambers in the water bath and adjusting the temperature of the system. After the system approached the temperature of the process, the pressure of the system was adjusted by adding anti-solvent to the chambers from the top. The anti-solvent flow rate was then adjusted by the metering valve at the exit. The required amount of ethanol was then added to the system by controlling the flow rate of each line. When using $CO_2$ as the anti-solvent, to achieve a $CO_2$-20 mol % ethanol mixture (ie, the $CO_2$:Ethanol molar ratio was 1:4), a flow rate of 3.4 mL/min and 15 mL/min of ethanol and $CO_2$, respectively, were passed through the static mixer. When using ethane as the anti-solvent, an ethane-30 mol % ethanol mixture was prepared using flow rates of 15 mL/min and 2.4 mL/min for ethane and ethanol, respectively.

After the system approached steady state, 0.1 mL/min insulin solution (100 mg/mL) was sprayed through the inner nozzle. The solution dispersed due to the high flow rate of the anti-solvent. Extraction of the water was facilitated from the droplets by the ethanol and fine insulin particles were formed. The metering valve 11 at the exit (ie, just downstream of the collection chamber outlet) is adjusted once precipitation commences such that the force exerted on the particles in the particle collection chamber by the dense gas flowing upwardly through the collection chamber is balanced by their weight (by gravity) so that the particles are in effect suspended within the collection chamber and not compacted. This effect is achieved with a flow rate of 15-20 mL/min. Other similar arrangements may be contemplated, such as collection chambers rotating about an axis to generate a force counter to that of the dense gas flowing through the collection chamber. Upon disconnection from the precipitation chamber, the collection chamber is depressurized and the product collected from both chambers, sealed in airtight containers and stored in the freezer (−18° C.).

When the entire apparatus is shut down, it has been found desirable that, after spraying, the solution ethanol and water residues were removed from the precipitate by passing the equivalent of 5 chamber volumes of ethane at operating pressure and temperature through the collection chambers. A small amount of ethane (about 10-50 mL) was also purged through the nozzle to remove any remaining solution. This process is necessary prior to the depressurisation of the system to prevent any droplets of the aqueous solution retained in the nozzle falling into the precipitation chamber, contacting the precipitated particles and causing agglomeration of the particles.

The effect of apparatus design on the characteristics of insulin particles precipitated from aqueous solution using ethane/30 mol % ethanol was examined at 25° C. and 155 bar. This is discussed further below.

It has been demonstrated that processing of insulin using ethane-ethanol provides for the retention of biological activity as indicated by the in vitro test for monomer content. Insulin processed with $CO_2$-ethanol experienced significant deactivation in this respect. In a single stage (prior art) apparatus, the particle characteristics of the $CO_2$-ethanol and ethane-ethanol processed material are similar as shown in Table 1. In the dual stage process (illustrated above and FIGS. 1, 7 and 8) the fine particle mass for the $CO_2$-ethanol system is similar to that obtained for the single stage process. A dramatic increase in this parameter was obtained for material processed with ethane-ethanol.

TABLE 1

Data from Single Stage and Dual Stage production units

| | Single Stage | | Dual Stage | |
|---|---|---|---|---|
| Anti-Solvent | $D_{(0.5,v)}$ | FPM(%) | $D_{(0.5,v)}$ | FPM(%) |
| Ethane-ethanol | 12.8 ± 1.0 | 20.0 | 4.8 ± 0.4 | 43.5 |
| $CO_2$-ethanol | 11.8 ± 1.6 | 20.3 | 8.2 ± 0.6 | 23.1 |

$D_{(0.5,v)}$ Median particle size based on volume (i.e. below which 50% of particles occur.
FPM(%) Fine Particle Mass - mass fraction of particles below 5 μm according to Cascade Impactor tests.

Whilst some reduction in $D_{(0.5,v)}$ occurs with the 2-stage $CO_2$-ethanol processing method, only 21.9% of this material can be dispersed to produce material less than 5 μm aerodynamic diameter. The material obtained using the 2-stage ethane-ethanol process has a dramatically reduced $D_{(0.5,v)}$, consistent with the 100% increase in the amount of material less than 5 μm aerodynamic diameter, as indicated in Table 1.

By way of another comparison, insulin was precipitated in a single-stage apparatus as nano-sized particles, most of which ranged in size from 50-500 nm using the apparatus represented in FIG. 1. Particle size distribution studies showed that the particles agglomerated to form micron-sized particles. The fine particle mass of the micronised powder precipitated was only 20%. The particles were collected on the filter assembly at the bottom of the chamber. Due in part to the high pressure and high flow rate of the anti-solvent, the powder was compacted and difficult to disperse. The fine particles that were not aggregated washed from the system by passing through the filter, therefore the yield was low (40%).

Insulin was also precipitated as nano-sized particles ranged in size from 50-500 nm using the apparatus represented in FIG. 1. The fine particle mass of insulin processed by the modified ASES apparatus was increased to 45%. The filter at the bottom of the first chamber was eliminated, producing a precipitate which was less compacted. The precipitate moves downward from the precipitation chamber and is carried upwardly part way through the collection chamber where gravity acts on it counter to the anti-solvent (dense fluid) flow direction, suspending the particles in the chamber, which minimises their compaction. Addition of the second (ie, particle collection) chamber enabled improved recovery of fine particle mass and increased the yield to 90%. FIG. 2 shows the aerodynamic particle size distribution of insulin powders in the single chamber and the dual chamber apparatus.

In order to determine whether the biological activity of the insulin was retained after the particle formation process, the biochemical integrity of the insulin powder was assessed using size exclusion chromatography. A protein-Pak 125 column (Waters, USA) was used for insulin. The mobile phase consisted of 50 mM sodium phosphate buffer at pH 3 with 300 mM sodium chloride.

The powder samples were dissolved to prepare 1 mg/mL solution in deionised water by gentle shaking for 10 minutes to have complete dissolution. The supernatant was filtered through 0.45 mm membrane filter and then injected into the HPLC column. The percent of monomer and the soluble aggregates were determined by comparing the peak area of both monomer and the high molecular weight soluble species in the sample with the peak area of a standard concentration of 1 mg/mL The percent of insoluble aggregates was estimated from the difference in the total peak area between the sample and the protein standard solution. The software Millennium 3.5 was used in the quantification of the monomer content. The HPLC spectrum of insulin is shown in FIG. 3. The monomer content of the sample was 99.5% thus providing an in vitro measurement illustrating that retention of biological activity was almost complete.

In order to determine the percentage of insulin that was deamidated by the process, a test of the insulin was performed using high performance liquid chromatography (HPLC). A reverse phase column (Symmetry® $C_{18}$, 5 μm packing, 4.6 mm×150 mm) was used to separate the deamidated from the non-deamidated insulin. The gradient method was used with eluents 0.1% trifluoroacetic acid/acetonitrile 26% to 33% and the flow rate of 1 mL/min. The absorbance was monitored at 280 nm. The percentage of deamido insulin was determined by comparing the peak area of the degradation product to the area of standard insulin containing the same concentration of insulin (2 mg/mL). The HPLC chromatogram for the separation of insulin and deamido insulin is depicted in FIG. 4. The percentage of deamido insulin determined from the HPLC chromatogram was 3.0, thus providing additional in vitro evidence for the retention of biological activity and chemical integrity of the molecule after particlisation by precipitation.

SEM images (FIG. 5) showed that insulin was precipitated as nano-sized particles ranging in size from 200 nm to 500 nm. These fine insulin particles may aggregate to form larger particles due to intermolecular interaction between the molecules. Analysing the particles by laser diffraction studies showed that the insulin powder agglomerated and possessed a median particle size of 5 μm (5000 nm).

In order to determine the aerosol performance of the collected fine protein particles, in vitro testing of the particles was assessed using a 5 stage Marple-Miller Impactor (Model 160, MSP Corporation, USA) with cut-off diameters of 10.0, 5.0, 2.5, 1.25, and 0.625 μm. The Marple-Miller impactor consisted of a stainless steel inlet throat, five impaction stages and an integral filter stage. The stages were previously coated with propylene glycol/methanol (50:50) to prevent particle bounce, thus minimising the probability of carry over of coarse particles onto lower stages.

A mass of 10-20 mg of insulin was weighed into a gelatin capsule (size 3, Park Davis, Australia) and was immediately dispersed by a powder inhaler device, Dinkihaler (Aventis, Frankfurt, Germany) into the Marple Miller Impactor at 60 L/min using a vacuum source (ERWEKA GMBH, Germany). The fraction of the protein recovered in each stage was calculated by measuring the absorbance of the protein solution against the absorbance of a standard 1% solution of insulin. The results of the assay method (measurement of relative UV absorption of a 1% solution) and the standard curves for insulin are indicated in Table 2.

TABLE 2

Protein assay methods and absorptivity value determined from the standard curve.

| Protein | Assay method | Standard curve |
|---|---|---|
| Insulin | UV absorbance at 275 nm | $A_{1\%} = 9.0$ <br> Conc. range = 0.01–0.1 % |

Figure 6:
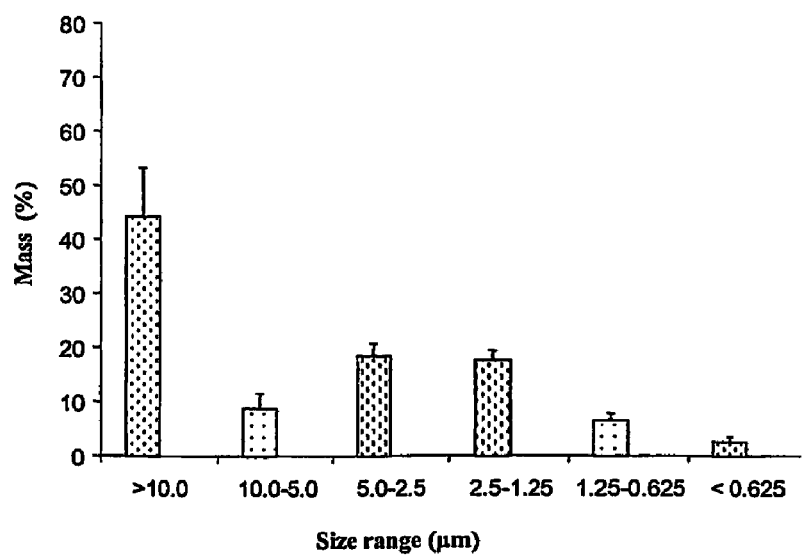
FIG. 6 shows a graph which represents the aerodynamic particle size distribution of insulin powder.

Insulin precipitated as nano-sized particles, was also agglomerated to micron-sized particles. The median particle size (determined by laser diffraction) was about 5 μm and the fine particle fraction (%<5 μm), determined by the Marple Miller Impactor, was at least 42%, as shown in FIG. 6. The fine particle mass (FPM) achieved is significantly greater compared with the values reported in the literature. The maximum FPM for insulin obtained by other methods was 10%.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. An apparatus for forming fine particles of a substance in a precipitation chamber comprising means to convey the fine particles from the precipitation chamber to at least one particle collection chamber disposed downstream of the precipitation chamber, wherein the particle collection chamber comprises an inlet and an outlet separate from the inlet, and wherein when the apparatus is in use, a carrying fluid exerting a first force on the fine particles conveys the particles into the particle collection chamber, the collection chamber being adapted such that a second balancing force is exerted generally towards the inlet on the fine particles adjacent the outlet.

2. The apparatus of claim 1, wherein the outlet is disposed above the inlet and the second force is gravity.

3. The apparatus of claim 1, wherein the particles are formed by contacting a non-gaseous fluid containing the substance with a dense fluid to expand the non-gaseous fluid in the precipitation chamber.

4. The apparatus of claim 1, further comprising at least two particle collection chambers in parallel with each other and each connectable in series with the precipitation chamber.

5. The apparatus of claim 4, wherein a first collection chamber is removable from the precipitation chamber without interrupting flow to at least a second collection chamber of particles from the precipitation chamber such that the fine particles collected in the first collection chamber are then recoverable from the first collection chamber.

6. The apparatus of claim 5, further comprising three or more collection chambers.

7. The apparatus of claim 3, wherein the dense fluid comprises a mixture of an anti-solvent and a modifying agent, the modifying agent modifying the polarity of the anti-solvent.

8. The apparatus of claim 3, wherein the dense fluid is cooled prior to entering the precipitation chamber through a co-axial nozzle, and the non-gaseous fluid containing the substance also enters the precipitation chamber through the co-axial nozzle.

9. A method of forming fine particles of a substance comprising: contacting a non-gaseous fluid containing the substance with a dense fluid to expand the non-gaseous fluid in a precipitation chamber, wherein the carrying fluid comprising the dense fluid and the non-gaseous fluid, exerts a first force on the fine particles to convey the particles into the particle collection chamber, the collection chamber being adapted such that a second balancing force is exerted generally towards the inlet on the fine particles adjacent the outlet.

10. The method of claim 9, wherein the outlet of the collection chamber is disposed above the inlet and the second force is gravity.

11. The method of claim 9, wherein the fine particles and dense fluid pass through the inlet of the collection chamber and flow of fluid through the outlet is adjusted to maximize the proportion of fine particles recoverable from the collection chamber.

12. The method of claim 9, wherein flow of fluid through the outlet is adjusted to maximize escape of the particles through the outlet with the fluid and/or to reduce aggregation and agglomeration of the particles.

13. The method of claim 9, for forming fine particles of pH sensitive substances and biologically active substances.

14. The method of claim 9, wherein the dense fluid includes a modifying agent present in an amount sufficient to absorb substantially all of the non-gaseous fluid of the non-gaseous fluid-biologically active substance solution.

15. The method of claim 14, wherein the modifying agent modifies the polarity of the anti-solvent and/or is an extractant for the non-gaseous fluid.

16. The method of claim 14, wherein both the non-gaseous gas fluid and the modifier are substantially inert to the substance.

17. The method of claim 9, wherein at least half of the fine particles produced have a particle size less than 10,000 nm.

18. The method of claim 14, wherein pressure of the dense fluid is such as to maintain the mixture of non-gaseous fluid and dense fluid as a single phase.

* * * * *

UNITED STATES PATENT AND TRADEMARK OFFICE
CERTIFICATE OF CORRECTION

| | | |
|---|---|---|
| PATENT NO. | : 7,641,823 B2 | Page 1 of 1 |
| APPLICATION NO. | : 10/497715 | |
| DATED | : January 5, 2010 | |
| INVENTOR(S) | : Foster et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1233 days.

Signed and Sealed this

Twenty-first Day of December, 2010

David J. Kappos
*Director of the United States Patent and Trademark Office*